US012768544B2

(12) United States Patent
Vantaggi et al.

(10) Patent No.: US 12,768,544 B2
(45) Date of Patent: Oct. 20, 2026

(54) EXTRACTOR HOOD FOR HOBS WITH AN AIR SANITISING CHAMBER

(71) Applicant: Faber S.p.A., Fabriano (IT)

(72) Inventors: Ermanno Vantaggi, Fossato di Vico (IT); Alberto Gasparini, Fabriano (IT)

(73) Assignee: FABER S.P.A., Fabriano (IT)

( * ) Notice: Subject to any disclaimer, the term of this patent is extended or adjusted under 35 U.S.C. 154(b) by 357 days.

(21) Appl. No.: 18/558,232

(22) PCT Filed: May 4, 2022

(86) PCT No.: PCT/EP2022/062000
§ 371 (c)(1),
(2) Date: Oct. 31, 2023

(87) PCT Pub. No.: WO2022/233945
PCT Pub. Date: Nov. 10, 2022

(65) Prior Publication Data
US 2024/0200788 A1 Jun. 20, 2024

(30) Foreign Application Priority Data
May 7, 2021 (IT) ........................ 102021000011711

(51) Int. Cl.
*A61L 9/20* (2006.01)
*F24C 15/20* (2006.01)

(52) U.S. Cl.
CPC ............ *F24C 15/2035* (2013.01); *A61L 9/20* (2013.01); *A61L 2209/12* (2013.01); *A61L 2209/14* (2013.01)

(58) Field of Classification Search
CPC .... F24C 15/2035; A61L 9/20; A61L 2209/12; A61L 2209/14
USPC ...................................................... 126/299 R
See application file for complete search history.

(56) References Cited

U.S. PATENT DOCUMENTS

| | | | | |
|---|---|---|---|---|
| 5,632,806 | A | 5/1997 | Galassi | |
| 10,918,758 | B1 * | 2/2021 | Bess ......................... | F24F 7/10 |
| 2004/0211321 | A1 | 10/2004 | Gibson | |
| 2008/0110339 | A1 * | 5/2008 | Kwok ................. | F24C 15/2035 95/79 |
| 2019/0240371 | A1 | 8/2019 | Benedek et al. | |

FOREIGN PATENT DOCUMENTS

| | | |
|---|---|---|
| CN | 107975831 | 5/2018 |
| CN | 112178729 | 1/2021 |
| DE | 202020106540 | 4/2021 |
| WO | 2012055504 | 5/2012 |

* cited by examiner

*Primary Examiner* — Avinash A Savani
(74) *Attorney, Agent, or Firm* — Volpe Koenig

(57) ABSTRACT

An extractor hood (1) for a hob of the type to be fitted above a hob in a kitchen, and including a first part or extractor part (3) in the vicinity of this hob, which part is connected to a second part or flue (4) having an extractor unit (5) which is connected to an exhaust for vapour extracted from said hob. A sanitising chamber (20) is provided into which air is extracted directly from the kitchen, and includes an extractor unit (21) and a source of radiation (22) which can sterilise this air extracted before it exits from this sanitising chamber (20).

22 Claims, 19 Drawing Sheets

EXTRACTOR HOOD FOR HOBS WITH AN AIR SANITISING CHAMBER

CROSS-REFERENCE TO RELATED APPLICATIONS

This application is a 371 National Phase of International Application No. PCT/EP2022/062000, filed May 4, 2022, which claims priority to Italian Patent Application No. 102021000011711, filed May 7, 2021, both of which are incorporated herein by reference as if fully set forth.

TECHNICAL FIELD

The subject of the present invention is an extractor hood for a hob.

Another subject of the present invention is an air sanitiser in the form of a stand-alone functional unit.

BACKGROUND

As is known, an extractor hood is used to extract water and grease vapour (hereinafter commonly indicated only by the term "vapour") from a hob on which food is prepared in a kitchen; said hood comprises a first part or extractor part which is in the vicinity of this hob, and is associated with a flue or second part which comprises an extractor unit (a fan supplied with electric power), and is connected to an exhaust for the vapour extracted from the hood. This discharge can take place into the kitchen once more, or outside the kitchen through an appropriate duct.

Conventional filters are provided to retain the impurities which are present in the vapour before it is discharged outside the extractor hood.

Extractor hoods are mainly of two types, i.e., placed above the hob (distant from, or close to, a wall of the kitchen), or incorporated in the hob itself, i.e., with the extractor part provided directly on the hob, and the second part with the fan placed below the hob. The present invention applies to the type of hoods placed above the hob, i.e., to wall, island, ceiling and freestanding hoods.

In recent times, the problem of purifying, sterilising or sanitising of the air in domestic environments has become very important, with these terms (purifying, sterilising and sanitising) meaning removal from the ambient air, or rendering inert, of the biological load of viruses, bacteria, spores, fungi, and other biologically active microorganisms. For this purpose, autonomous sanitising devices are known, provided with an extractor unit which extracts the ambient air into a body of the device where this air encounters UV radiation with an appropriate wavelength (in band C, or with wavelengths between 200 and 280 nm, preferably between 250 and 265 nm, indicated as UVC radiation) emitted by an appropriate source (defined by one or more UVC lamps); this air is thus purified or sanitised before being expelled from the device and emitted once more into the environment.

However, these sanitising devices take up space, they must be connected autonomously to the electrical mains network of the environment in which they are used, and they can therefore be an obstacle for the movement of people in this environment. In addition, when they are used, they must be placed on a shelf or on the floor, consequently also being aesthetically unattractive. On the other hand, when they are not being used, they are placed inside a piece of furniture, or in a different environment for storage, which involves the use of other space, and the fact of having to move the sanitising device again, with the risk of damaging the delicate source of UVC radiation and its conventional control electronics.

SUMMARY

The objective of the present invention is to provide an extractor hood for hobs of the aforementioned type, which also makes it possible to carry out the function of sanitising the air.

In particular, the objective of the present invention is to provide an extractor hood of the aforementioned type, which makes it possible always to have the possibility of sanitising the air of the environment (kitchen) in which it is placed, and which does not take up further space in this environment, such as to be problematic for the movement of people or for the appearance of the environment itself.

A further objective is to provide an extractor hood of the aforementioned type which is however efficient both in extracting the vapours from the hob and in extracting the air from the environment to be sanitised.

Another objective is to provide an extractor hob of the aforementioned type where the sanitised air is different from the vapour extracted from the hob (wet and carrying grease and particles) which vapour could be deposited on the UVC source and reduce the efficiency thereof in sanitising the air.

Another objective is to provide an air sanitiser as a stand-alone functional unit, which air sanitiser can be used independently from an extractor hood, e.g., in a kitchen environment, especially when an extractor hood without air sanitiser has already been installed.

These objectives and others, which will become apparent to persons skilled in the art, are achieved by an extractor hood having one or more of the features disclosed herein and by means of the air sanitiser having one or more of the features disclosed herein.

In an embodiment of the extractor hood or the air sanitiser, the source of UV radiation can be an UV lamp, which provides a simple a cost-effective way of realisation. Said lamp can be devised as an LED.

In another embodiment of the extractor hood or the air sanitiser, the source of UV radiation is ozone free, which is preferably with respect to a user's health.

In yet another embodiment of the extractor hood or the air sanitiser, the source of UV radiation can emit UVB radiation with wavelengths between 285 and 315 nm, which can be effective against particular types of germs.

In yet another embodiment of the extractor hood said sanitising chamber can be secured on the second part or flue of the extractor hood. This may allow retrofitting of existing extractor hoods with a sanitising chamber.

In still another embodiment of the extractor hood said sanitising chamber is placed inside the second part or flue of the extractor hood or the sanitising chamber is integrated with the second part or flue of the extractor hood. Such embodiments may be preferred from an esthetical point of view.

In still another embodiment of the extractor hood the sanitising chamber is placed transversely to the second part or flue of the extractor hood, such that the air treated moves orthogonally to the exhaust for the vapour extracted by the extractor hood, wherein the aperture for entry of the air into the sanitising chamber and the exhaust aperture of the sanitising chamber are placed on opposite sides with respect to the flue.

This may result in a design which requires only little extra space for the sanitiser chamber and which can efficiently separate the air streams of the hood and the sanitiser, respectively.

In still another embodiment of the extractor hood the sanitising chamber is placed on an upper side of the first part, said upper side facing away from said hob in an installed state of the extractor hood.

This enables a particularly efficient separation of the air streams from the hood and from the sanitiser, respectively.

In yet another embodiment of the extractor hood the aperture for entry of the air into the sanitising chamber and the exhaust aperture of the sanitising chamber are both placed in an upper side of the sanitising chamber, which upper side faces away from said upper side of the first part.

This can help to optimise separation of the air streams from the hood and from the sanitiser, respectively.

In a highly preferred embodiment of the extractor hood, the extractor hood is devised as a ceiling hood and has an underside of said first part or extractor part, which underside is intended to face a cooking hob in an installed state of the extractor hood and presents at least one intake for the vapour, wherein the sanitising chamber is integrated in said first part on at least one side of the intake, such that both an aperture for entry of air to be sanitised and said exhaust aperture are devised in said underside.

Thus can be provided a ceiling hood with additional sanitising functionality, a design of which does not differ from commonly known ceiling extractor hoods.

In another highly preferred embodiment of the extractor hood, a power supply and a functioning of the sanitiser chamber is/are independent from a power supply and a functioning of the extractor hood, wherein preferably simultaneous use of the extractor hood and the sanitiser chamber is prevented by respective control means thereof. Is helps to avoid a disturbance of the air flows between the two apparatuses (hood and sanitiser) and to prevent cooking fumes or vapours from being sucked in by the sanitiser, which may shorten a lifetime of the UV radiation source and/or decrease a sanitising efficiency thereof.

In a further embodiment of the air sanitiser, a mechanical filter is inserted in the air inlet to reduce fouling of the UV lamp and guarantee sanitising effectiveness. The same feature can be present in the extractor hood at said aperture that permits entry of air into the sanitiser chamber.

Preferably, in a further embodiment of the air sanitiser, said cabinet or housing is devised for fixing to a ceiling or wall of a room. This allows easy integration of the air sanitiser into a home environment, in particular in a kitchen.

BRIEF DESCRIPTION OF THE DRAWINGS

For better understanding of the present invention, purely by way of non-limiting example, the following drawings are attached, in which.

DETAILED DESCRIPTION

Figure 1:
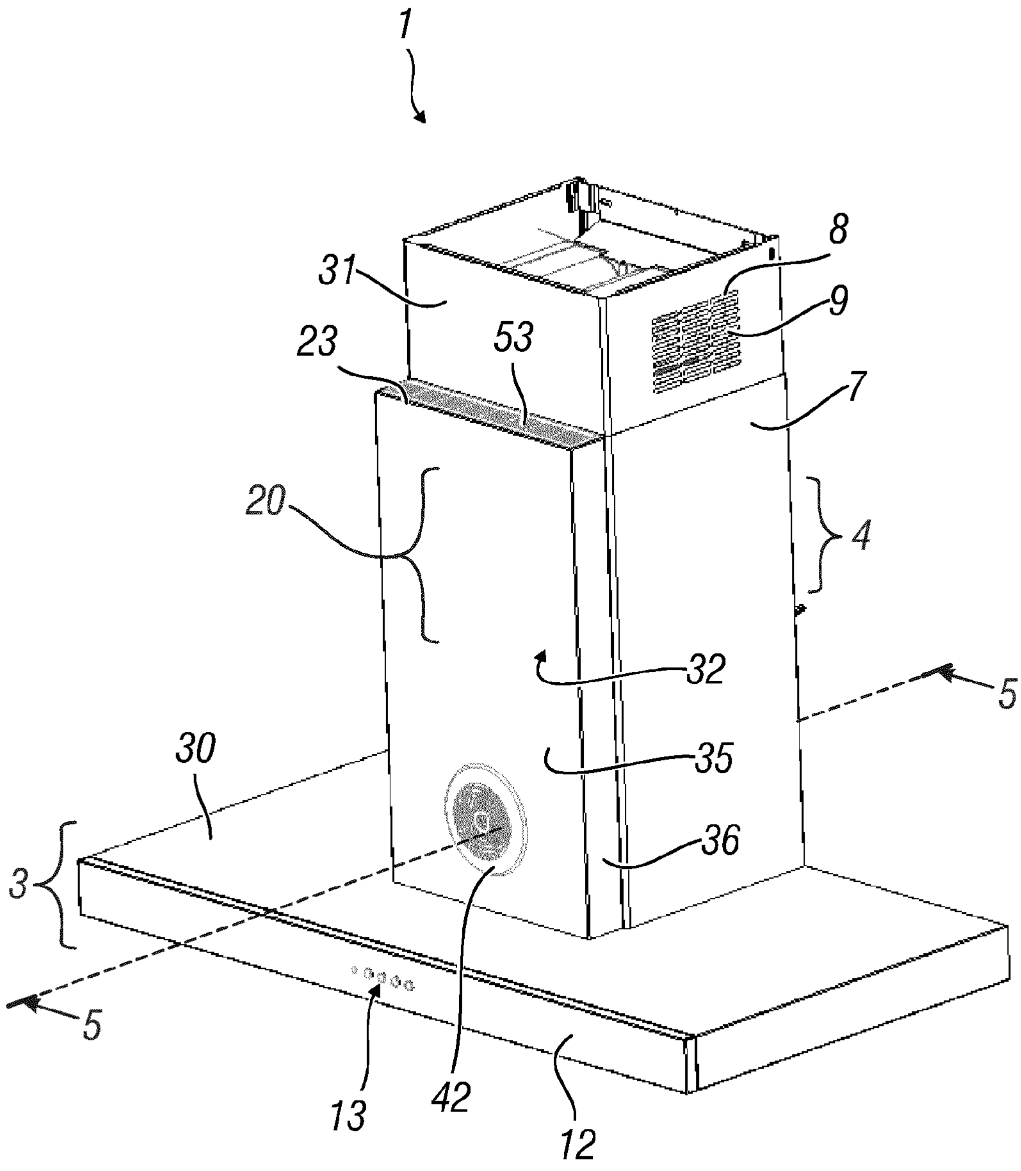
FIG. 1 shows a perspective view of a first extractor hood according to the invention.

The said FIGS. 1 through 17C show an extractor hood 1 for a kitchen hob, of the type which can be placed above this hob (not shown), which hood is also in contact with a wall of the kitchen, and can re-emit the vapour extracted from this hob (understood as water and grease vapour) into the environment after the usual filtering of the vapour through known filters 2 placed at a first part or extractor part 3 of the hood. This first part is placed at the end of a second part or flue 4 of the extractor hood 1 comprising a conventional extractor unit or fan 5 (with its own electric motor), which can permit collection of the vapour from the hob, and discharge thereof through an expulsion section 7 of the flue 4 provided with openings 8 on which grids 9 are placed.

It will be appreciated that an exhaust pipe, to take the vapour extracted and filtered outside the kitchen in a known manner, can be connected to an inner part 10 of the flue.

A free face 12 of the first (extractor) part 3 is provided with a user interface 13, which can permit command and control of the operation of the extractor hood 1 by means of conventional control electronics 15 inside the first part 3 at the interface 13.

The extractor hood 1 comprises a sanitising chamber 20 provided with an extractor unit 21 to extract ambient air into said chamber and direct it to a source of radiation 22, for example UVC or UVA, inside the chamber 20 itself, and then to at least one aperture 23 for discharge of the air extracted and sanitised (by the UVC source 22).

The air is thus reintroduced into the environment (kitchen) from which it has been extracted.

More particularly, and with reference to FIGS. 1-5, the sanitising chamber 20 is outside the first and second parts 3 and 4 of the extractor hood 1. For example, this chamber is placed on a flat face 30 of the first extractor part 3, and is in contact with a frontal face 31 (with reference to a possible user using the hood) of the second part or flue 4. The sanitising chamber 20 has a box-shaped body 32 which is hollow inside at 33, and, in the example in the figures (see in particular FIG. 3) has a frontal portion 35 which also delimits laterally (with sides 36) this sanitising chamber 20 and a shoulder or rear part 37. This rear part 37 is secured, for example by means of screws (not shown), to the sides 36 of the frontal portion 35; it has a surface 39 (facing towards the inside or towards the cavity 33 of the sanitising chamber 20) which preferably has a mirror finish in order to reflect better the UV rays emitted by the source 22 inside the cavity 33; preferably, an inner surface 40 of the frontal portion 35 also has a mirror finish.

Both the frontal portion 35 and the rear portion 37, which constitute the box-shaped body 32, are made of metal, preferably of stainless steel and/or galvanised metal plate and/or aluminium alloy. In fact, as well as providing better reflectance to the UV, and thus better radiating/germicidal efficiency on the surfaces and on the air which passes through the sanitising chamber, metal materials do not undergo deterioration associated with exposure to the UV rays, in particular the UVC rays, as occurs for example in the case of components made of some types of polymers.

Alternatively, the frontal portion 35 can be secured directly on the face 31 of the second part or flue 4 of the hood, which thus also acts as a functional part of the sanitising chamber (it closes it on one side).

The frontal portion 35 of the sanitising chamber has a hole or aperture 41 on which a grid 42 is placed, and behind which, inside the aforementioned cavity 33, there is placed the extractor unit 21 defined by an electric fan 43 controlled by means of the user interface 13 and the control electronics 15 of the extractor hood 1.

Figure 2:
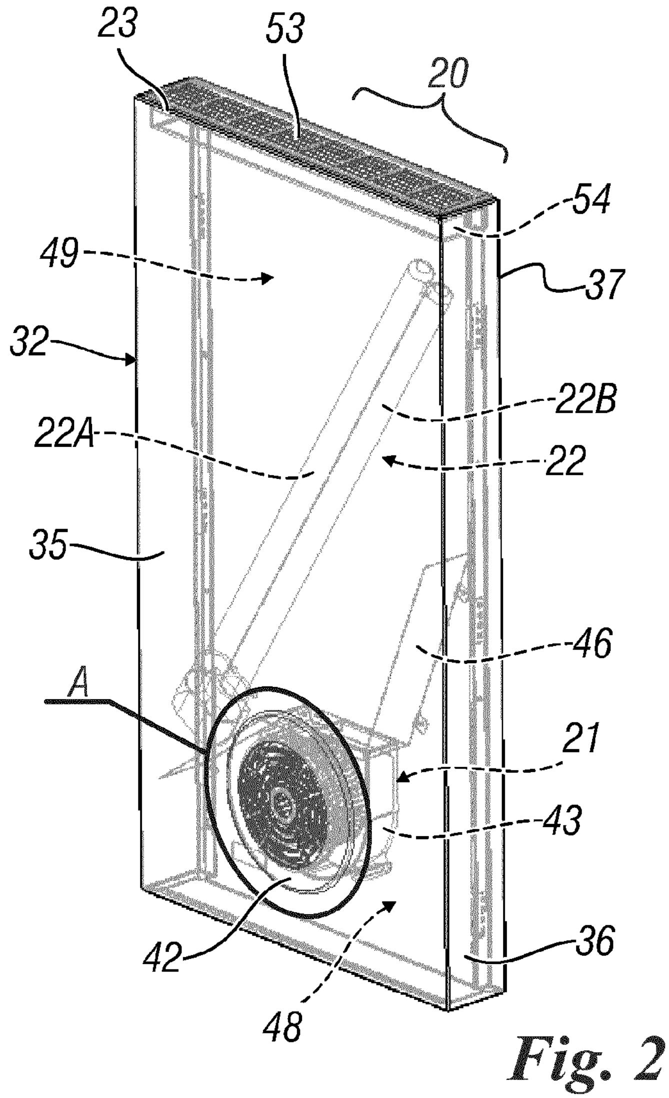
FIG. 2 shows a perspective view of a component of the hood in FIG. 1.
Figure 2A:
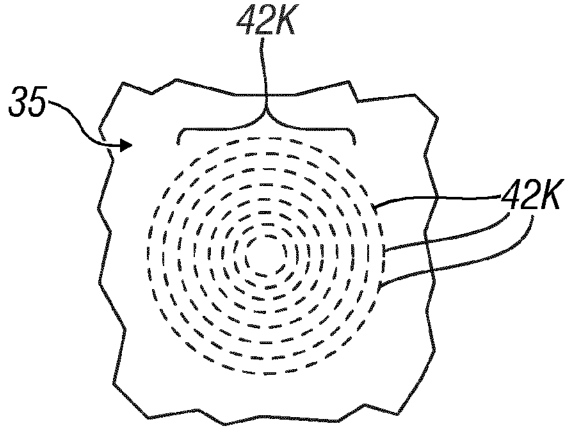
FIG. 2A shows the part indicated as A in FIG. 2, enlarged, with a different embodiment of the invention.

As shown in FIG. 2A, by way of example, the grid 42 can be replaced by a plurality of through holes 42K provided in the frontal portion 35, at which, inside the sanitising chamber 20, the electric fan 43 is placed.

Inside the cavity 33 of the sanitising chamber, a divider 46 is preferably placed, which is provided with an aperture 47 through which the electric fan 43 directs the air extracted to the UV source 22 for sterilisation/sanitising thereof. The divider 46 thus subdivides the cavity 33 into two spaces, i.e., an extractor space 48 where the electric fan 43 is placed, and a sanitising space 49 where the UV source 22 is present. This permits better extraction action by the fan, and better efficiency of the UV sources.

By this means, there is separation between the air extracted by the fan from the outside through the apertures or the grid 42 present in the frontal portion 35 of the sanitising chamber, and the area of delivery of the air from the "mouth" of the fan 43, which then exits from the sanitising chamber as will be described hereinafter.

Figure 11:
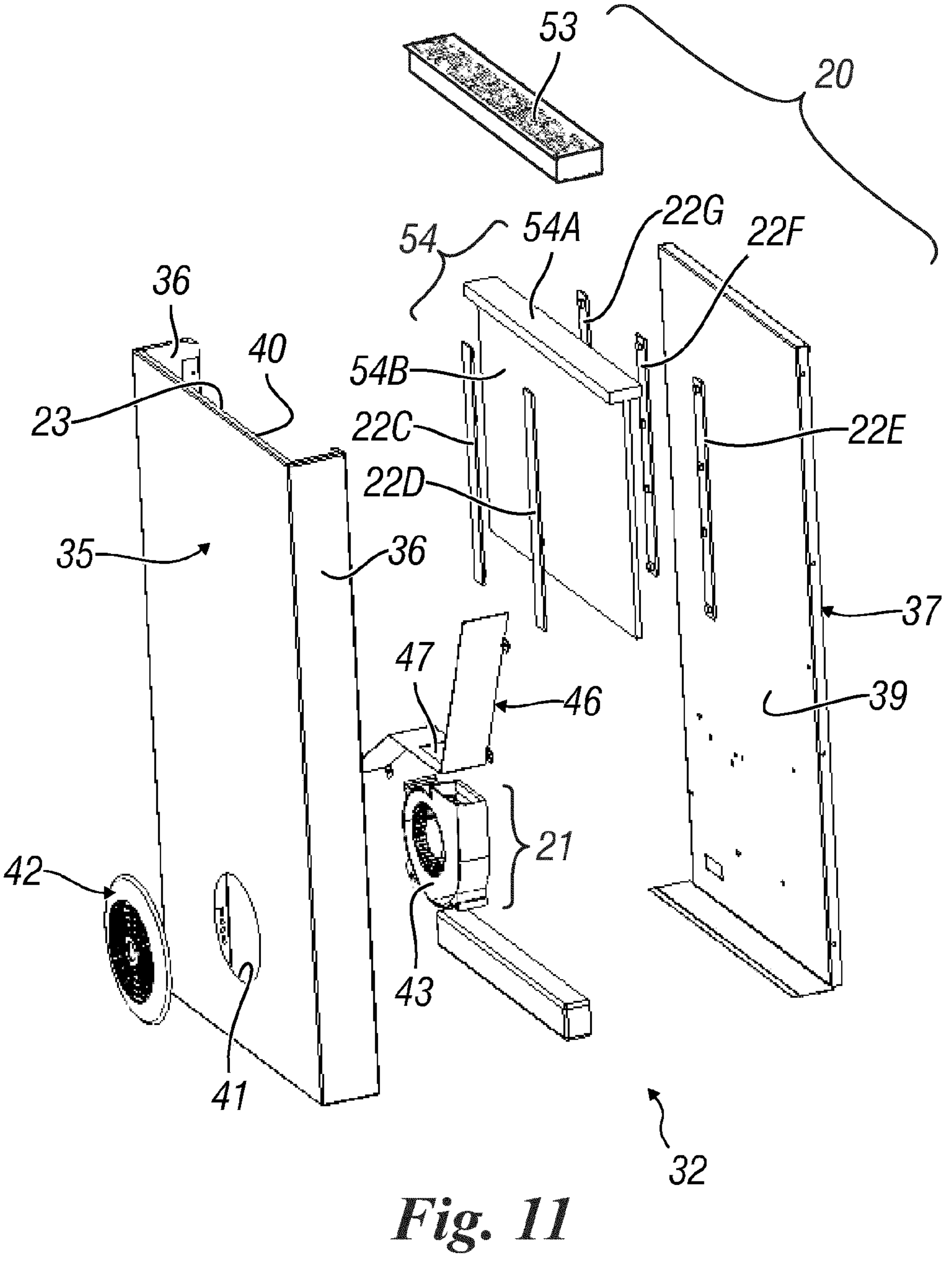
FIG. 11 shows a view similar to that in FIG. 3, but with different components.

According to one embodiment, the UV source 22 is a UVC source, defined in the example in FIGS. 1-10 and 12-14 by two LED lamps 22A, 22B, and in FIG. 11 by an LED strip 22C-22G, and it emits radiation which is preferably in the interval between 200 and 280 nm, preferably 222 nm, or between 250 and 265 nm. It is also possible to use LEDs of the UVA type with emission of radiation with wavelengths of between 360 and 415 nm, preferably between 365 and 380 nm. This is in order to be efficient in sanitising of the air which laps the source.

This air exits from the exhaust aperture 23 provided on an upper side (i.e., a side which is distant from the extractor part 3) of the sanitising chamber 20. On this aperture there is placed a grid 53 and preferably a filter 54 which can be a further filter for sanitising the air, or an activated charcoal filter, or a perfumed filter, or any other type of filter.

In a preferred embodiment, a type of filter is used with a deposit based on $TiO_2$ (for example, a filter with a ceramic or polymer or metal base) in various forms (such as anatase, rutile, etc.); the action of filters of this type is photocatalytic and therefore germicidal on the surfaces of the filter, and consequently on the air which passes through it. This action is activated by the emissions of UV radiation, in particular by the UVA rays which have an optimum wavelength interval. The filter of the type with a deposit or treatment based on $TiO_2$ can also have a particular geometry with a surface of contact with the air of passage which is increased in order to increase the efficiency thereof. For example, this filter can have a portion 54A at the grid 53, and a portion 54B in the vicinity of the source of radiation (UVC, or preferably UVA) 22, such as to adopt a transverse cross-section in the form of an elongate "T". This is shown for example in FIG. 11, where parts already described with reference to FIGS. 1-5 are indicated with the same numerical references. In this figure, the UV sources are defined by LED strips which are secured on the surfaces 39 and 40 of the frontal portion 35 and the rear part or shoulder 37.

By this means, thanks to the invention, by intervening on the user interface 13 of the hood 1, it is possible to activate the extractor unit 21 and the UV source 22 such as to extract air into the sanitising chamber 20 and purify it, sterilising it before it is expelled from the aperture 50 of this sanitising chamber.

In the solution in FIGS. 6-10, where parts corresponding to those of the figures already described are indicated by the same numerical references, the sanitising chamber 20 is inside the extractor hood 1, and in particular inside its second part or flue 4. The chamber 20 has the box-shaped body 32 secured on the inside of an end portion 56 of the second part or flue 4; the body has its frontal face 35 placed on a wall (for example, again the frontal wall 31) of said second part or flue 4. The hole 41 of the frontal face 35 of the box-shaped body 32 faces towards one of the apertures 8 (with the grid 9) of this flue, and receives air through it.

In the solution in question, the extraction space 48 is placed above the sanitising space 49, which is separated from the space 48 by the divider 46 with the aperture 47; however, the positions of these spaces 48 and 49 can also be inverted.

Inside the lateral walls 36 of the box-shaped body 32 there are present the apertures 23 on which there can be placed filters 54 (similar to the one described above in relation with FIGS. 1-5), with said apertures facing corresponding apertures 8 of the second part or flue 4 of the extractor hood 1.

As in the solutions of FIGS. 1-5, the air from the kitchen is extracted by the extractor unit 21, it is directed through the aperture 47 to the sanitising space 49, it passes onto the LED lamps 22A, 22B, and is expelled from the apertures 60 and from those 8 of the flue 4 after having been sanitised.

It is wished to show that the sanitising chamber 20 is an element or component which is inseparable from the extractor hood 1: in fact, this chamber 20 is connected to the control electronics 15 of the hood, and its operation is controlled by these electronics.

The sanitising chamber 20, whether it is inside or outside the second part or flue 4 or is disposed in another position relative to this part or to the first part 3, is always controlled by the interface 13 of the extractor hood 1.

Thus, it is apparent that this sanitising chamber 20 is part of the extractor hood. Consequently, it does not take up space in the environment in which the chamber 20 is placed, and it does not need to be moved away when it is not being used.

As an alternative to the simple on/off button or timer button (which switches the cycle off automatically after a certain amount of time), in order to control the switching on/off of the sanitising chamber 20, the user interface can have a series of push-pull buttons or touch buttons by means of which, using the control electronics 15, it is possible to control various sanitising cycles: each of these cycles is characterised by a specific speed of the fan and by a cycle time with automatic switching off. An example could be constituted by a so-called night cycle corresponding to a reduced air flow rate (fan in silent mode) and a longer sanitising cycle because of the flow rate, and on the other hand a standard cycle could have a greater air flow rate and reduced cycle time.

FIGS. 12-15 show a vertical hood 1 provided with a sanitising chamber 20 interposed along the path of exit of the vapour from the flue 4. In these figures (where parts corresponding to those of the figures already described are indicated by the same numerical references), the sanitising chamber is placed after the extractor unit or fan 5. On a first side 75, this chamber has a lateral aperture for extraction of the air with a grid 42, and on the opposite side 76 it has the exhaust aperture provided with a grid 53 in the vicinity of which the UV source 22 is present; after the divider 46 there is placed the extractor unit 21, which discharges the air axially through an exhaust aperture 23 (provided with a grid 53). The sanitising chamber 20 also has an aperture 87 (with a grid 88) placed inside the flue 4, for passage of the exhaust of the fan 5. In this embodiment, the sanitising chamber 20 is thus disposed orthogonally to the flow of the vapour which is moved by the fan 5 and extracted by the extractor part 3 (which is inclined relative to the flue 4 by an angle other than 90°) and by a lower aperture 89 of the flue 4.

Thus, the air to be sanitised is always collected outside the flue 4 from the environment (kitchen), and is moved orthogonally to the exhaust for the vapours extracted by the fan 5. This air does not pass via the vapour extraction, which takes place from the lower frontal inclined (area 3) area of the hood (through the aperture 89) via the fan 5. These vapours can be discharged outside the environment by means of a pipe which is connected to the aperture 87, or, the air which is filtered by the hood (including with the assistance of charcoal filters) is readmitted into the room (and in this case the flue 4 is not present above the sanitising chamber 20).

A description has been provided of various embodiments of the invention. However, others are also possible in order to obtain an extractor hood in conformity with the context of protection defined by the following claims.

Figure 12:
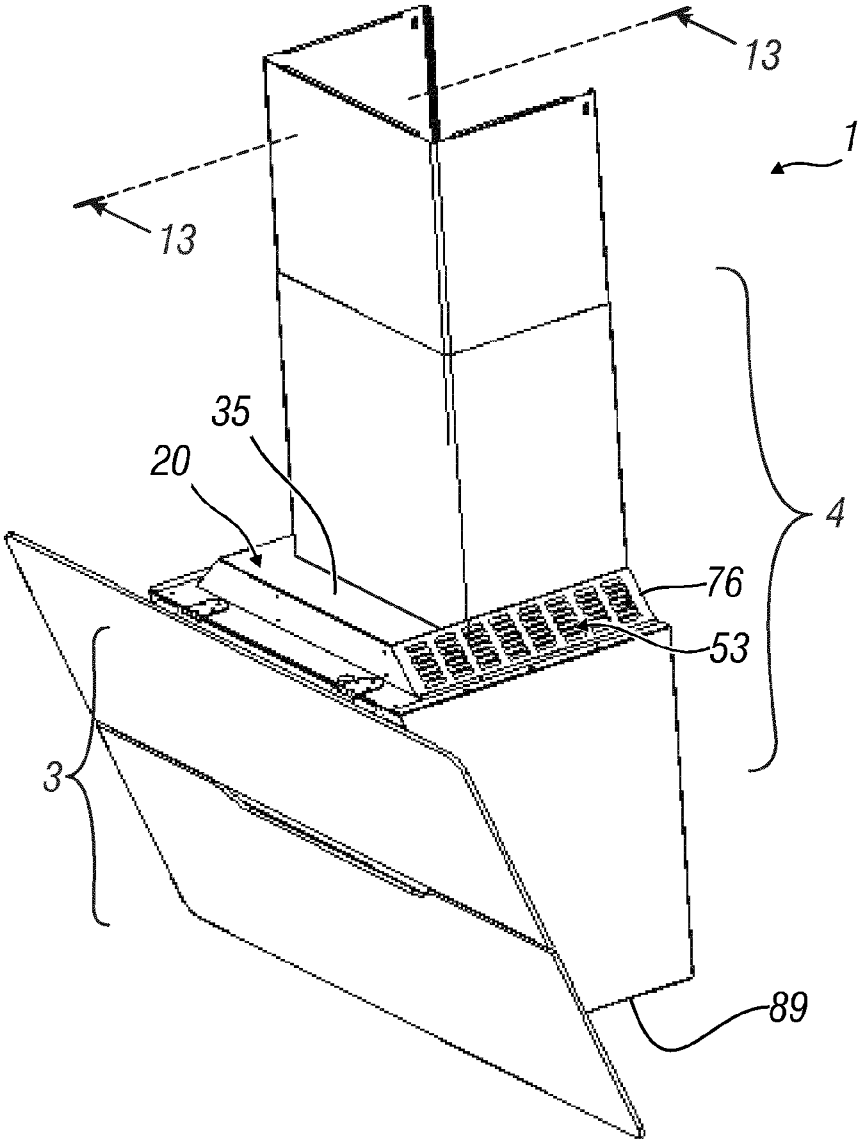
FIG. 12 shows a perspective view of a vertical wall hood according to the invention.
Figure 16A:
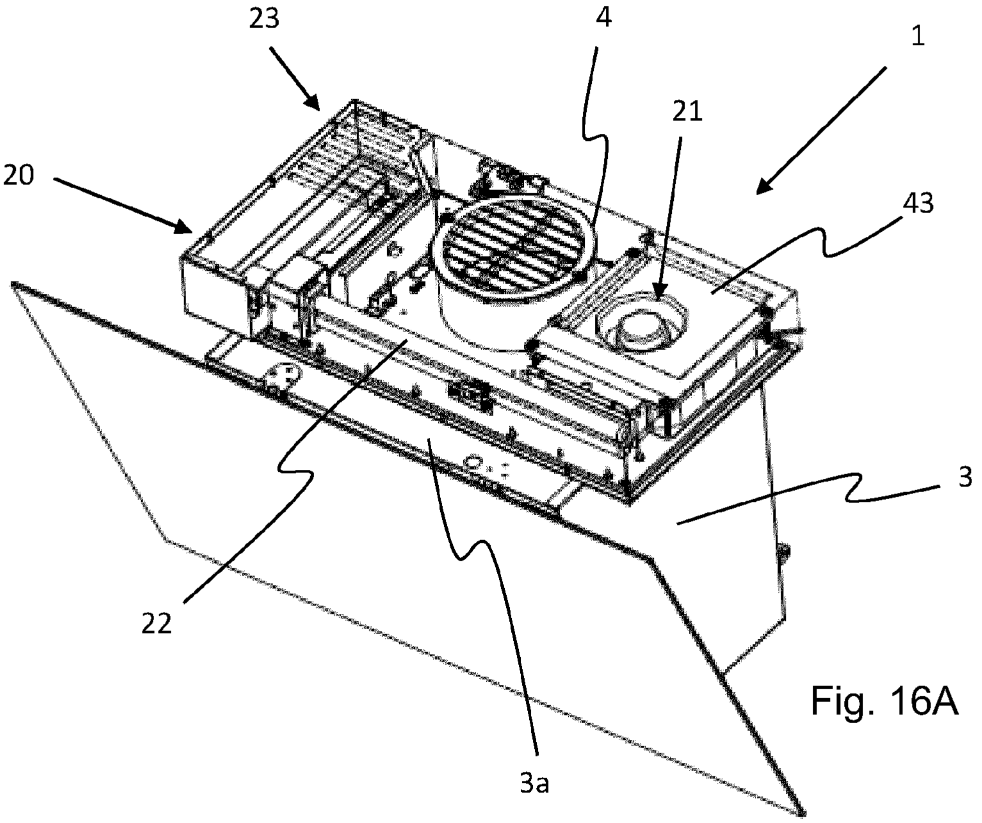
FIGS. 16A and 16B show a variation of the design of the extractor hood according to FIG. 12.
Figure 16B:
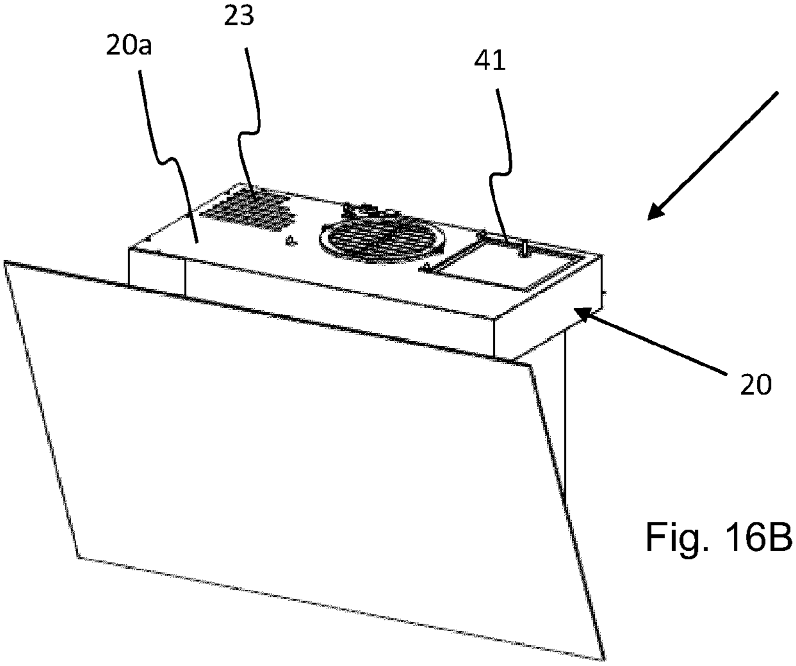

FIGS. 16A and 16B show a variant of the design of an extractor hood 1 according to the invention as shown in FIG. 12. Elements that are identical or at least have the same effect also bear the same reference numerals.

Figure 3:
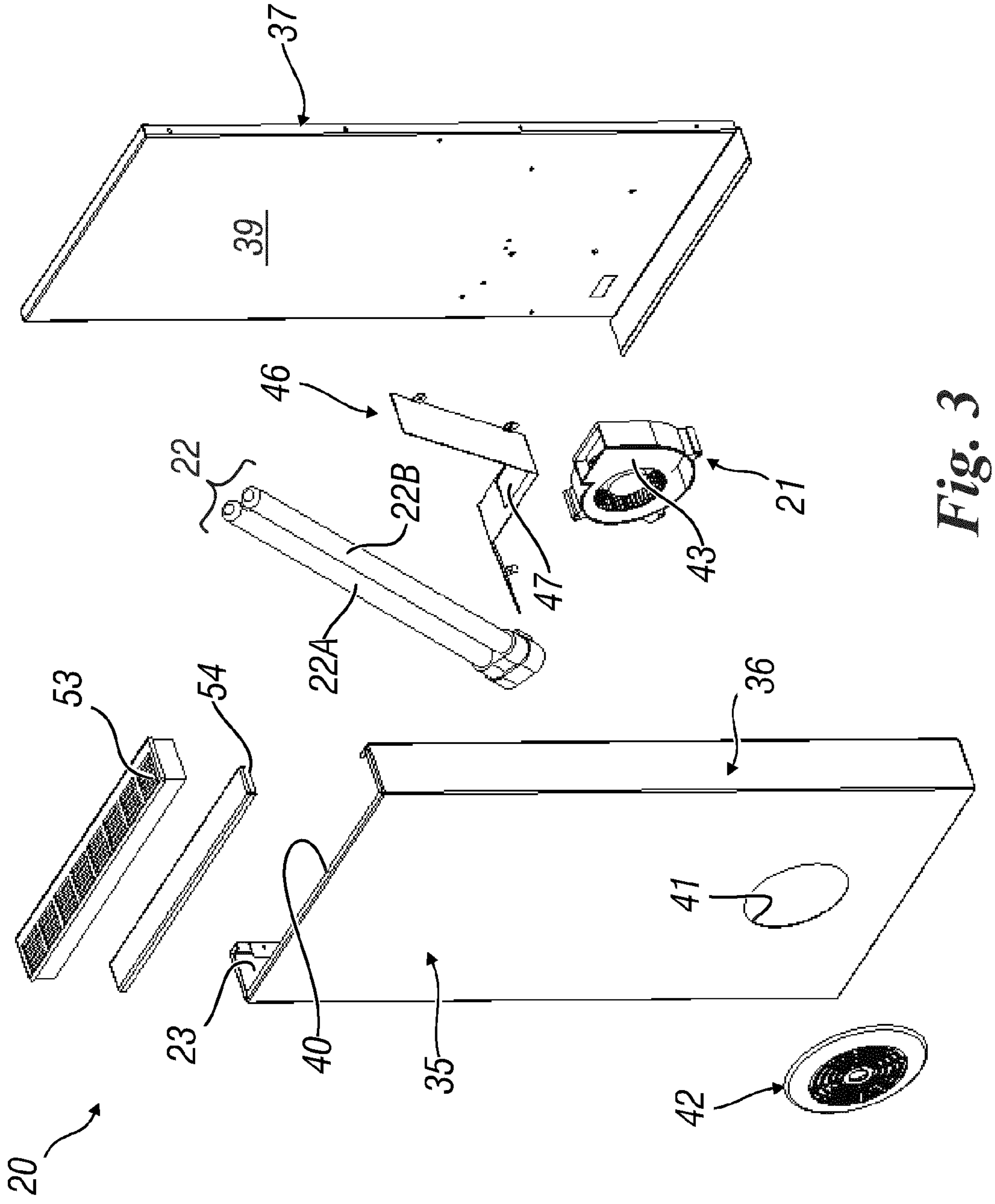
FIG. 3 shows an exploded perspective view of the component of FIG. 2.
Figure 4:
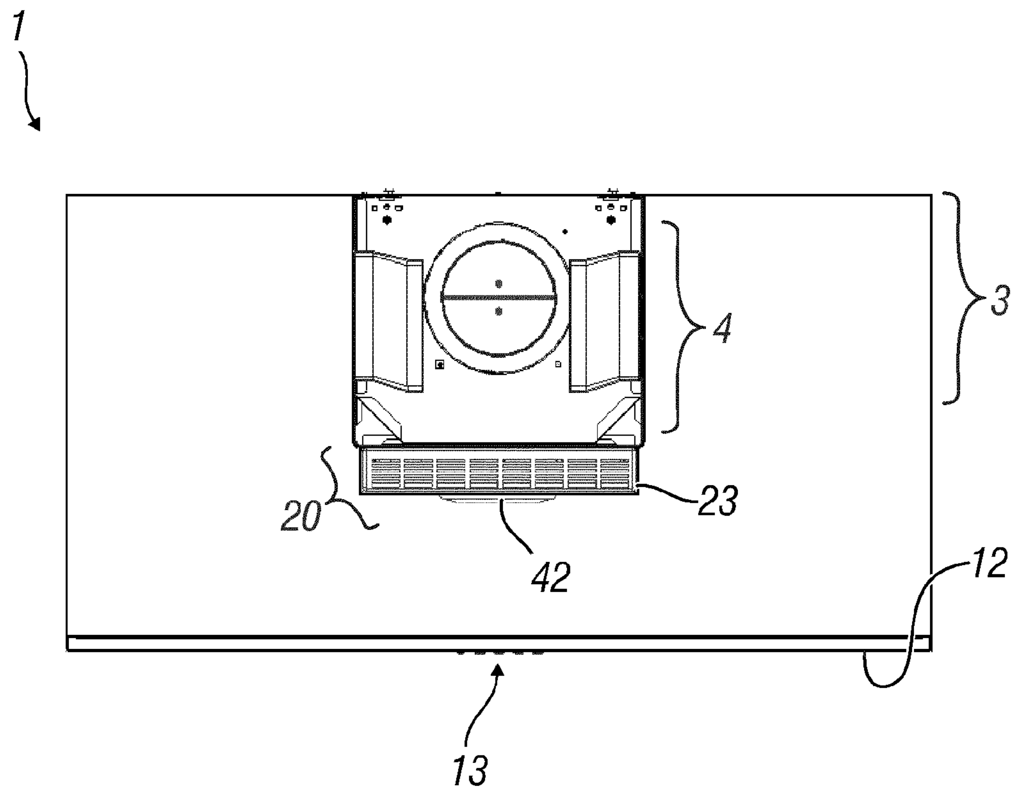
FIG. 4 shows a view from above of the hood in FIG. 1.
Figure 5:
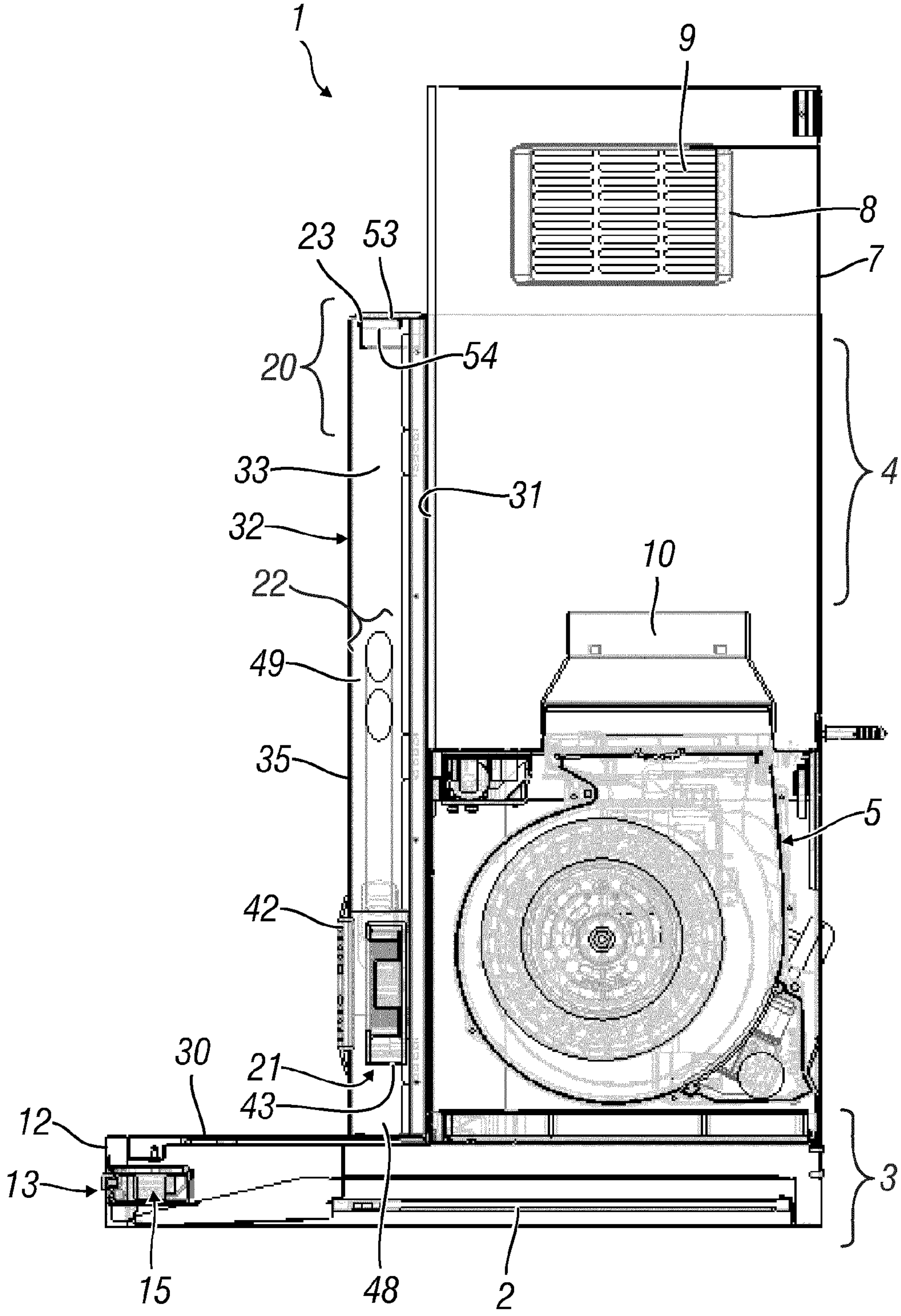
FIG. 5 shows a view in cross-section according to the line 5-5 in FIG. 1.
Figure 6:
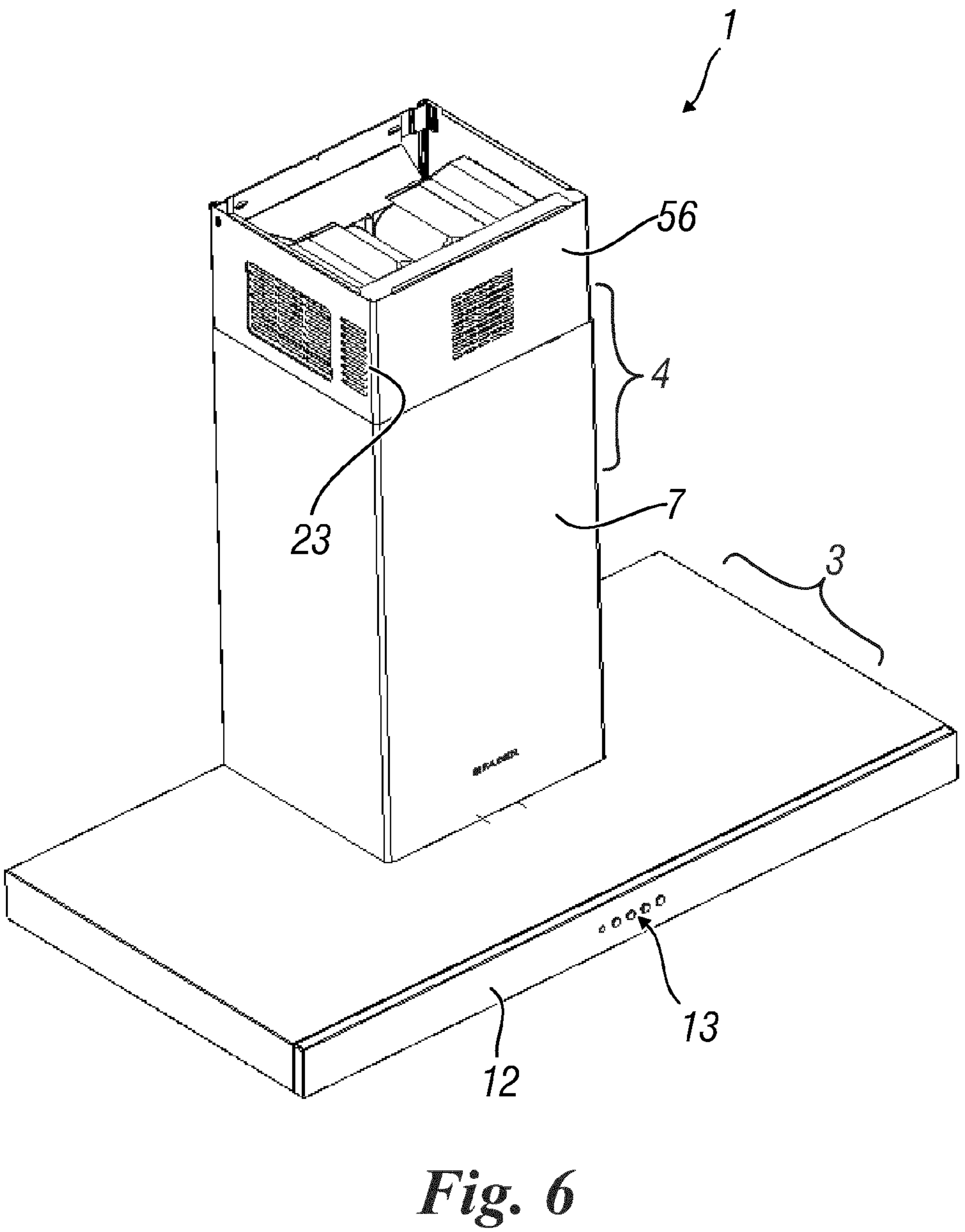
FIG. 6 shows a perspective view of a second extractor hood.
Figure 7:
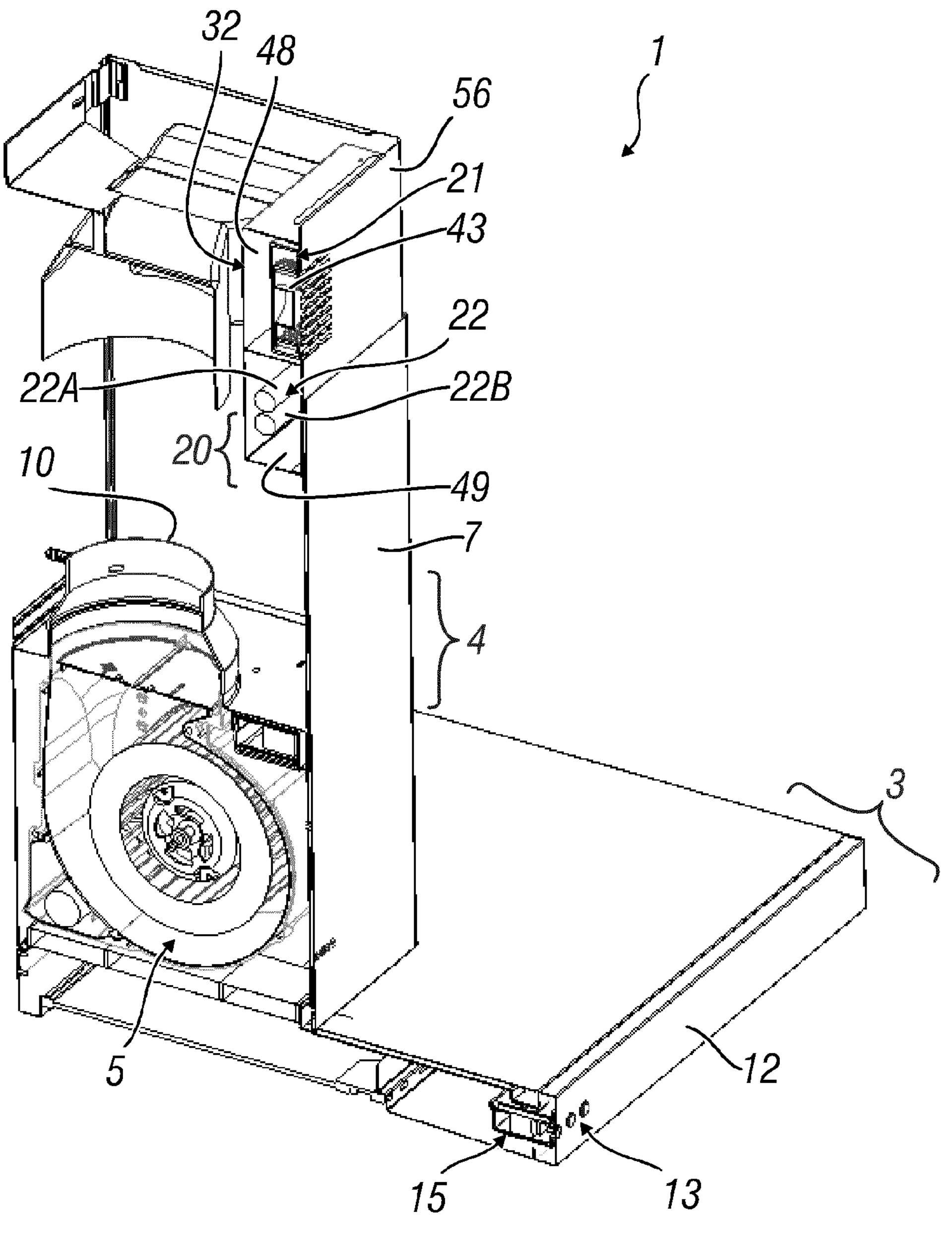
FIG. 7 shows a view in cross-section according to the line 7-7 in FIG. 6.
Figure 8:
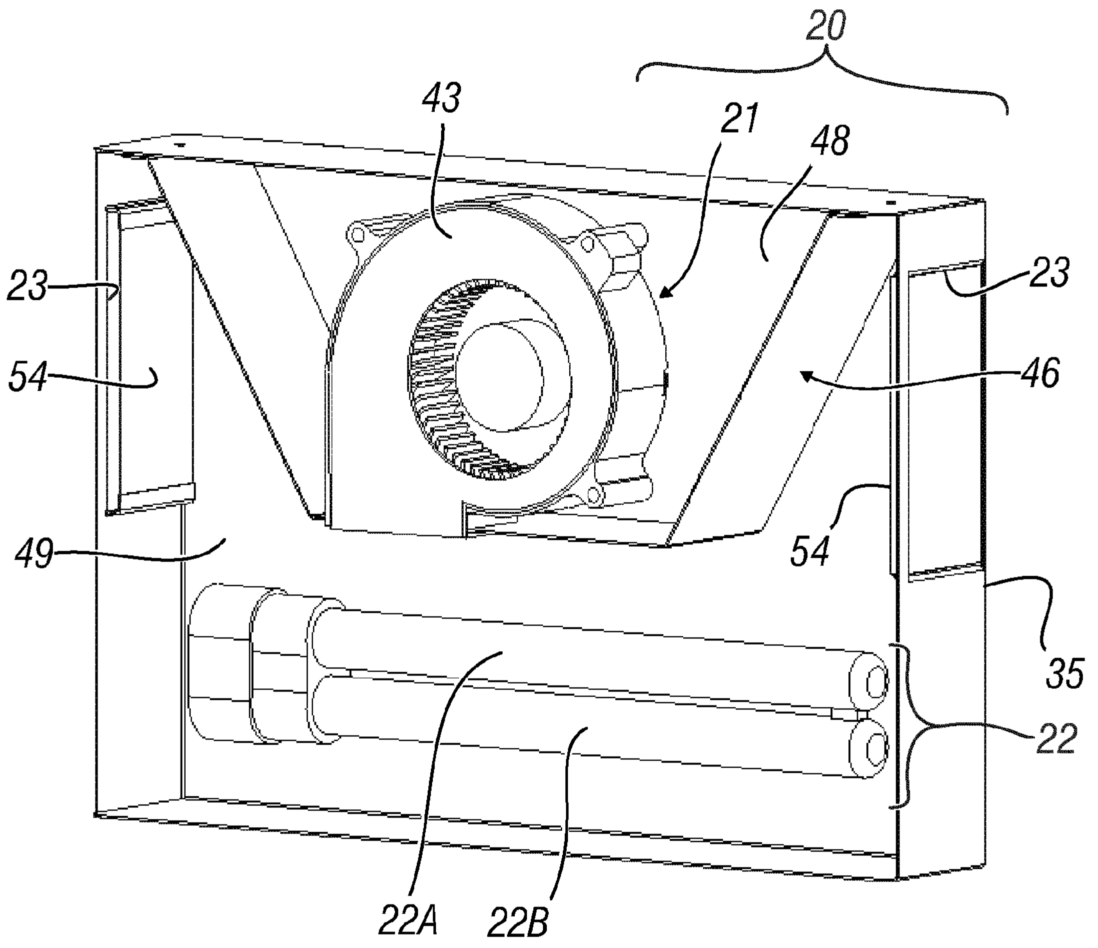
FIG. 8 shows a perspective view of a component of the hood in FIG. 6, with a part removed for greater clarity.
Figure 9:
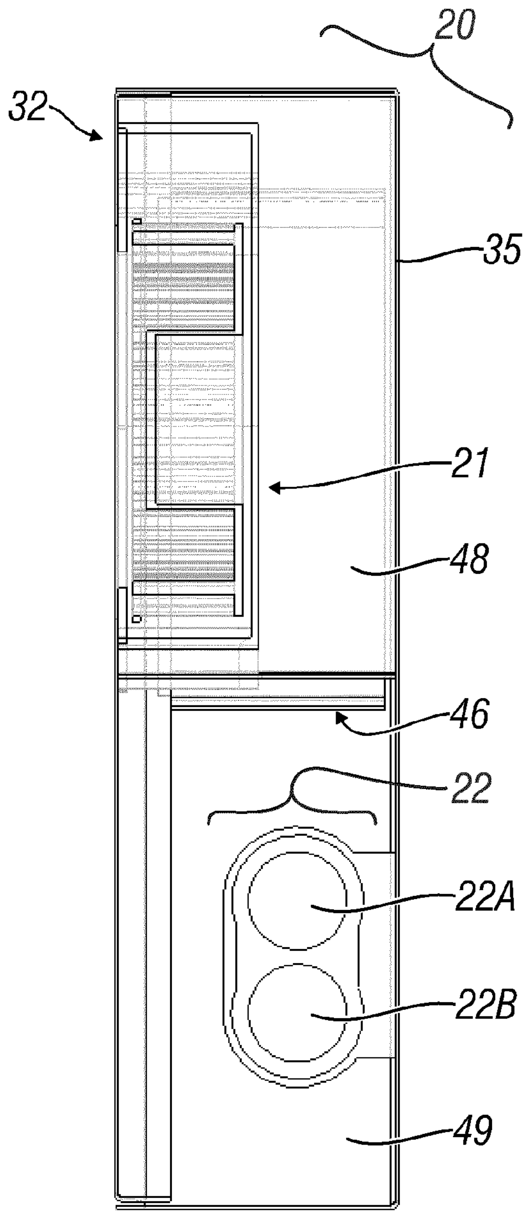
FIG. 9 shows a view in cross-section, according to the line 9-9 in FIG. 8, of the complete component.
Figure 10:
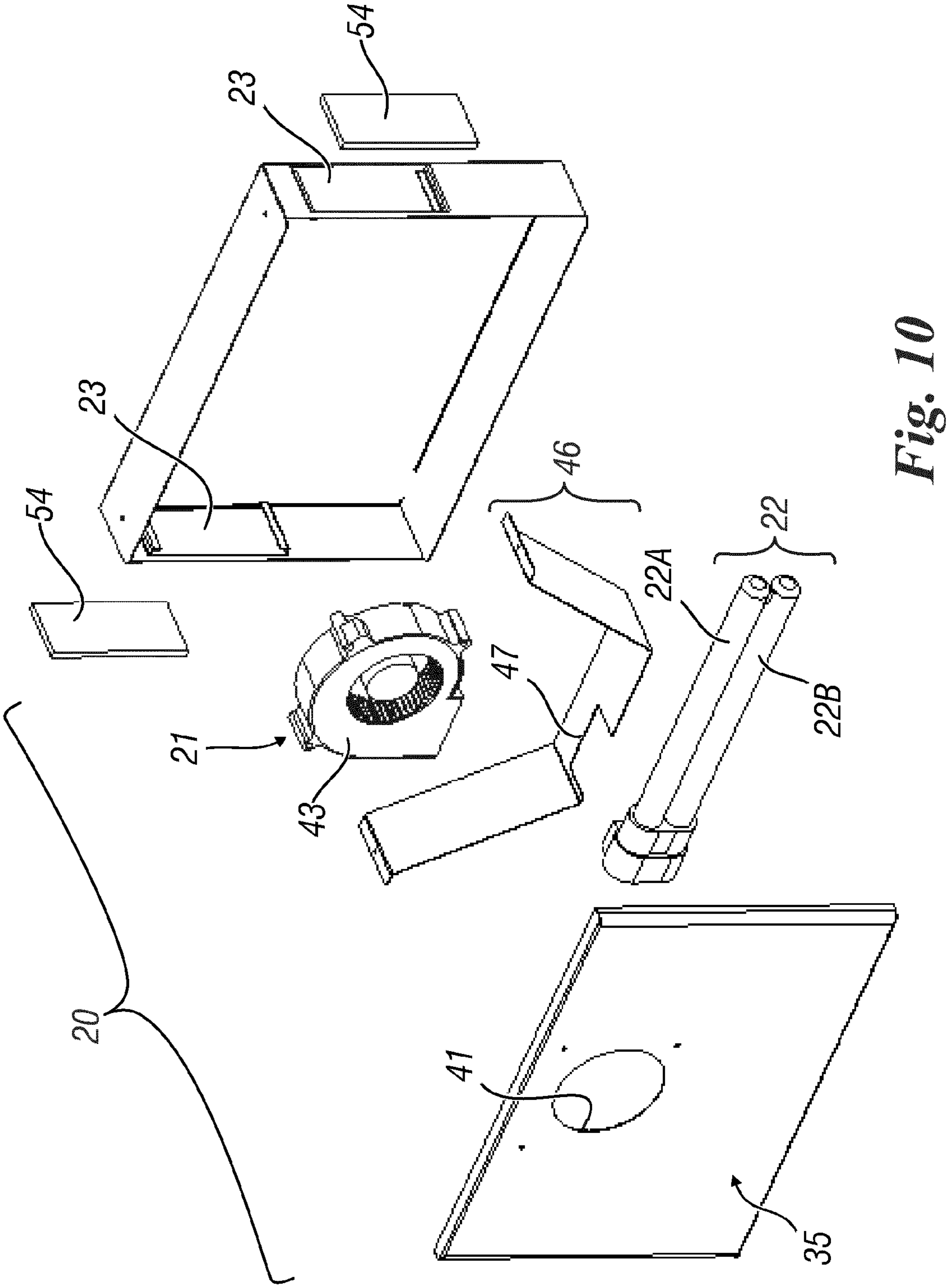
FIG. 10 shows an exploded perspective view of the component in FIG. 8.

Essential differences between FIGS. 16A and 16B on the one hand and FIG. 12 on the other hand are the arrangement of the openings for the entry of the air to be treated into the air sanitiser (or sanitising) chamber 20 and for the exit of the treated air from the air sanitiser (or sanitising) chamber 20, which openings are again provided with reference numerals 41 and 23, respectively (cf. FIG. 3).

Both openings or apertures 23, 41 are located in an upper side 20*a* of the air sanitiser (or sanitising) chamber 20, which upper side 20*a* faces away from an upper side 3*a* of the first part 3. Reference numeral 22 again indicates the source of the (UV) radiation. The opening or aperture 41 for entry of the air into the sanitising chamber 20 and the exhaust aperture 23 of the sanitising chamber 20 are placed on opposite sides with respect to the flue 4, cf. FIG. 12.

Figure 17A:
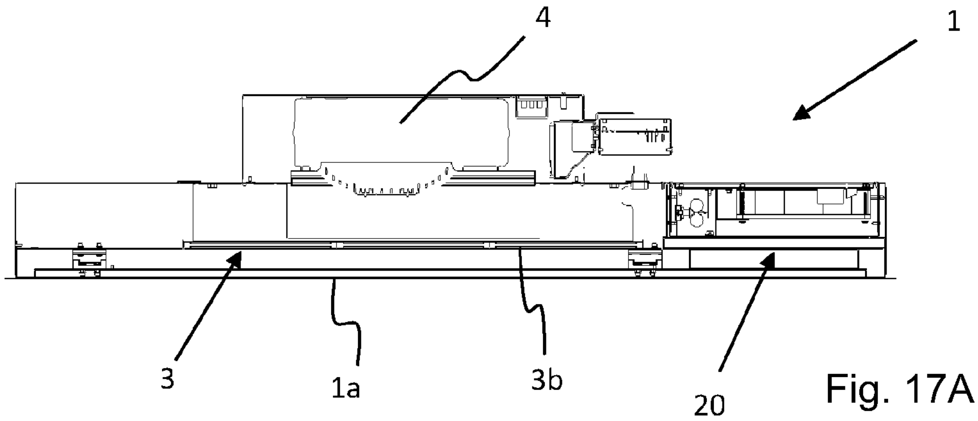
FIG. 17A to 17C show a further embodiment of the extractor hood according to the invention, which is intended for ceiling mounting.
Figure 17B:
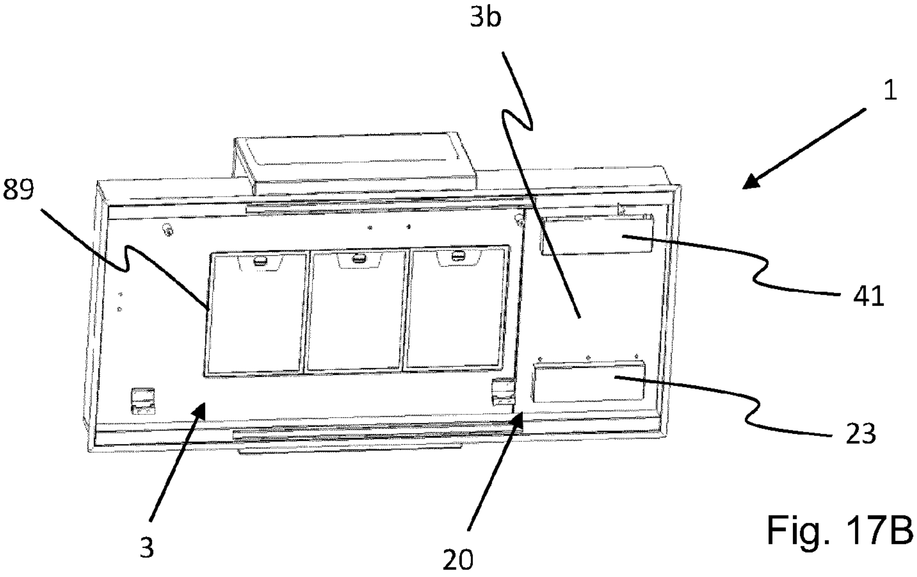
Figure 17C:
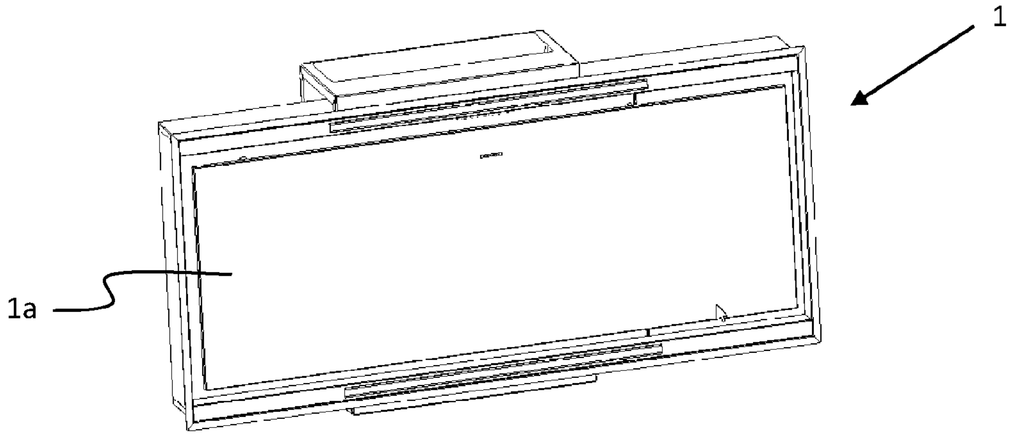

FIGS. 17A to 17C show an embodiment of the extractor hood 1 that is particularly suitable for ceiling mounting. The ceiling would be arranged correspondingly above the extractor hood 1 in FIG. 17A.

Figure 13:
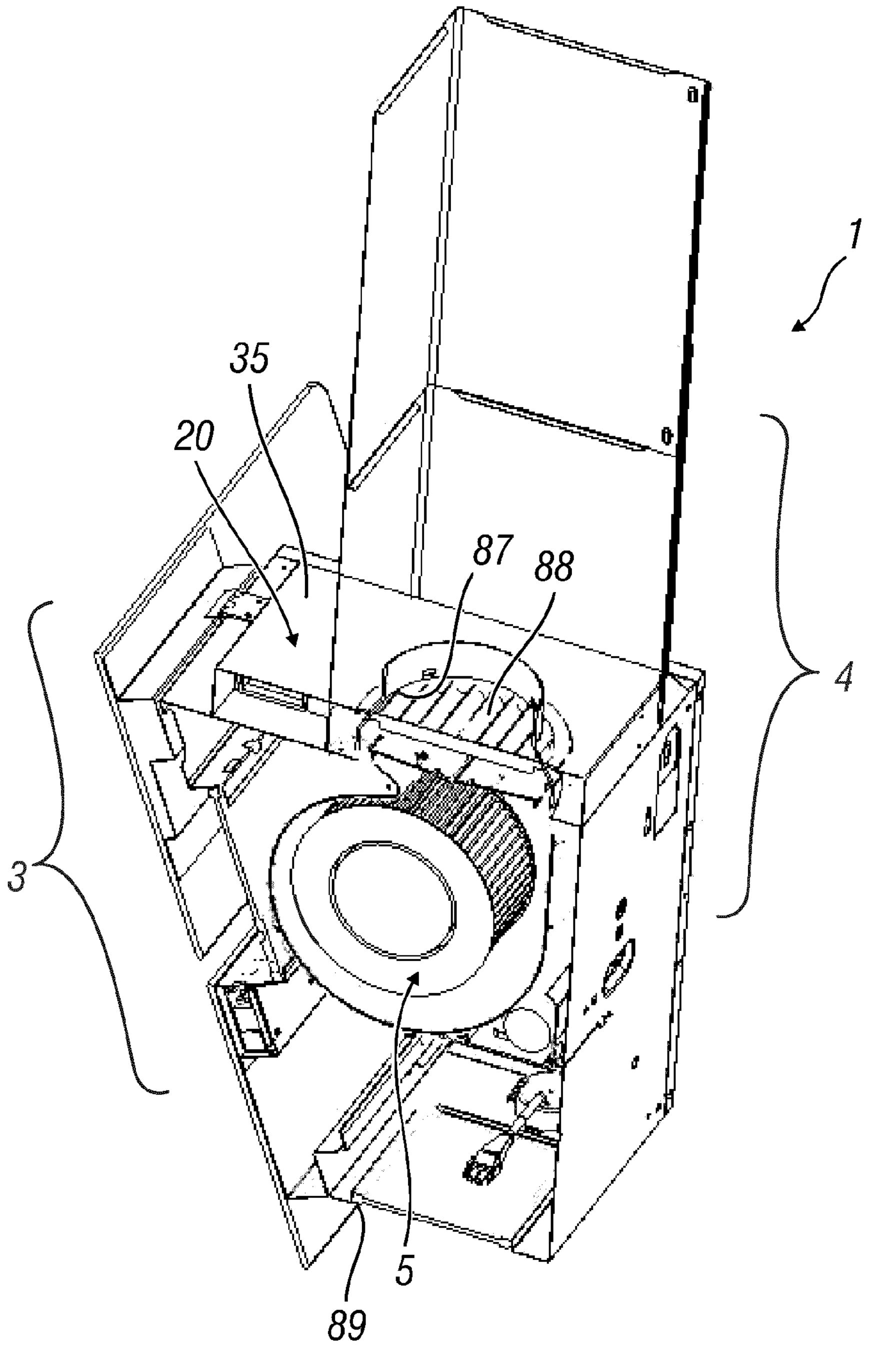
FIG. 13 shows a cross-section according to the line 13-13 in FIG. 12.
Figure 14:
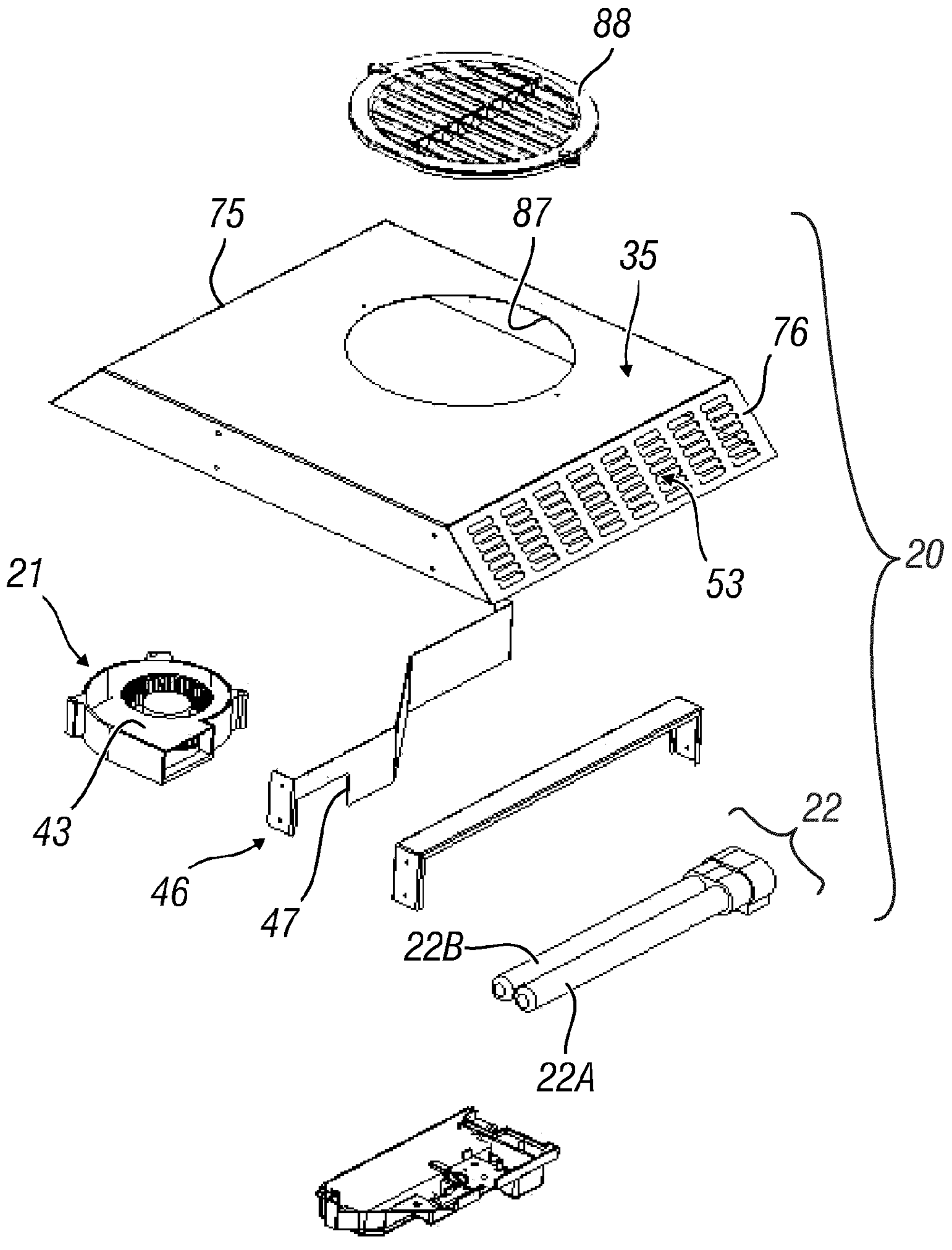
FIG. 14 shows an exploded perspective view of a detail of the hood in FIG. 12.
Figure 15:
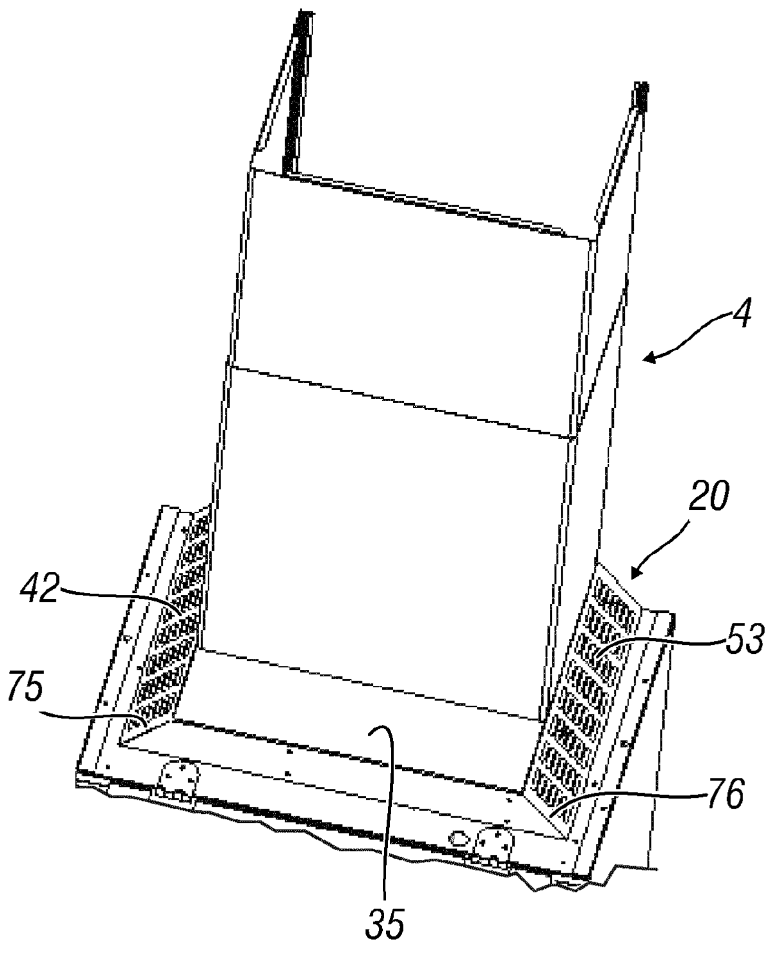
FIG. 15 shows a partial perspective view from another angle of the hood in FIG. 12.

As can be seen in particular from FIGS. 17A and 17B, whereby FIG. 17B provides a view of the extractor hood 1 from below, in this embodiment the air sanitiser (or sanitising) chamber 20, which can be devised as described above, is arranged laterally next to or in extension of the first part 3 of the extractor hood 1, which first part 3 presents a lower aperture 89 of the flue 4, cf. FIGS. 12, 13. Reference numerals 23, 41 again designate the air outlet and the air inlet of the air sanitiser (or sanitising) chamber 20, respectively. These two openings 23, 41 are arranged in an underside 3*b* of said first part 3 of the extractor hood 1, which underside 3*b* in an assembled state of the extractor hood 1 faces or is to face a hob (not shown).

FIG. 17C shows a state of the extractor hood 1 in which the first part 3, its underside 3*b* and the openings 23, 41 are hidden behind a detachable cover element 1*a*.

Figure 18A:
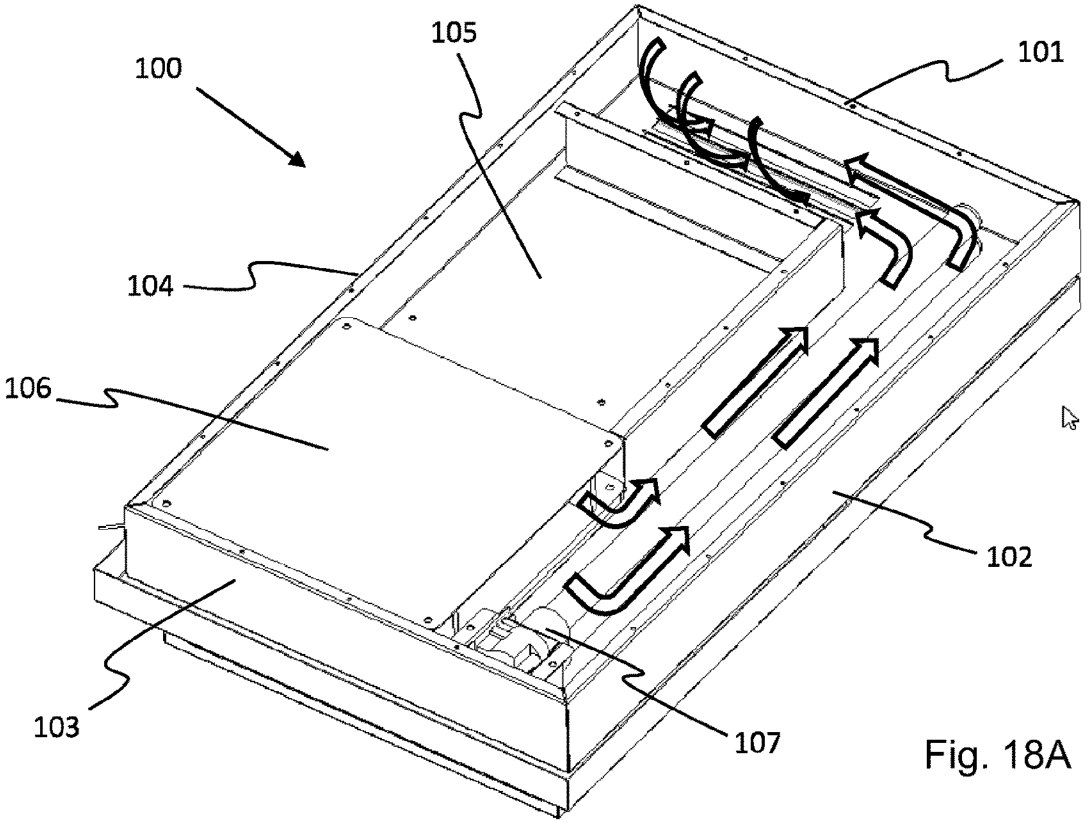
FIGS. 18A and 18B show an air sanitiser for ceiling mounting according to the invention.
Figure 18B:
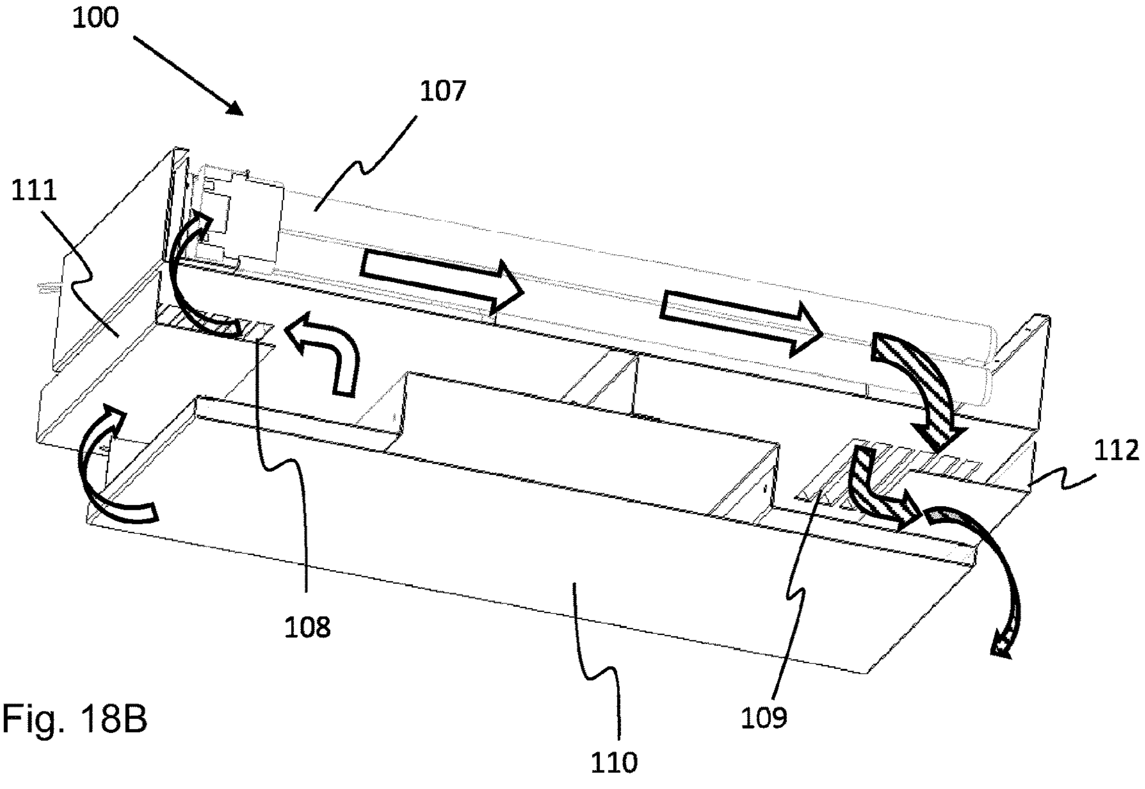

FIGS. 18A and 18B show a stand-alone air sanitiser or air sanitiser unit 100 for ceiling mounting. The air sanitiser unit 100 comprises a box-shaped housing with four side walls 101 to 104 and a bottom or front wall 105, which housing may be open towards the ceiling. Reference numeral 106 denotes a fan or a corresponding fan housing. Reference numeral 107 denotes a source of (UV) radiation arranged within an L-shaped duct for guiding the air (to be treated or treated). The air or its flow is symbolised by arrows in FIGS. 18A and 18B, whereby in particular hatched arrows indicate the treated air.

The fan 106 comprises an impeller (not visible) that is rotatable around a fan axis (cf. FIG. 19*b*), such that the air is drawn in along said axis and discharged orthogonally with respect to said axis, and the source of (UV) radiation 107 is located downstream of said fan 106.

As can be seen in particular from FIG. 18B, the housing has an opening 108 for the entry of the air to be treated (inlet) and an opening 109 for the exit of the treated air (outlet). Both openings 108, 109 are formed in the bottom wall 105 of the housing and thus face away from the ceiling in a mounted state.

Preferably, the air sanitiser unit 100 has, in mechanically operative connection with the bottom wall 105 of the housing, a cover element 110 which is approximately T-shaped in cross-section and covers the openings 108, 109, a distance remaining between the cover element 110 and the bottom wall 105 of the housing which allows the air (to be treated or treated) to pass through. In this way, the cover element 1*a* shields the inlet 108 and the outlet 109 from the environment while leaving a fluid connection between said inlet 108 and outlet 109, respectively, and the environment. In addition, lateral closing elements 111 and 112 are provided in each case, so that in each case the S-shaped air flow shown in FIG. 18B results.

Figure 19A:
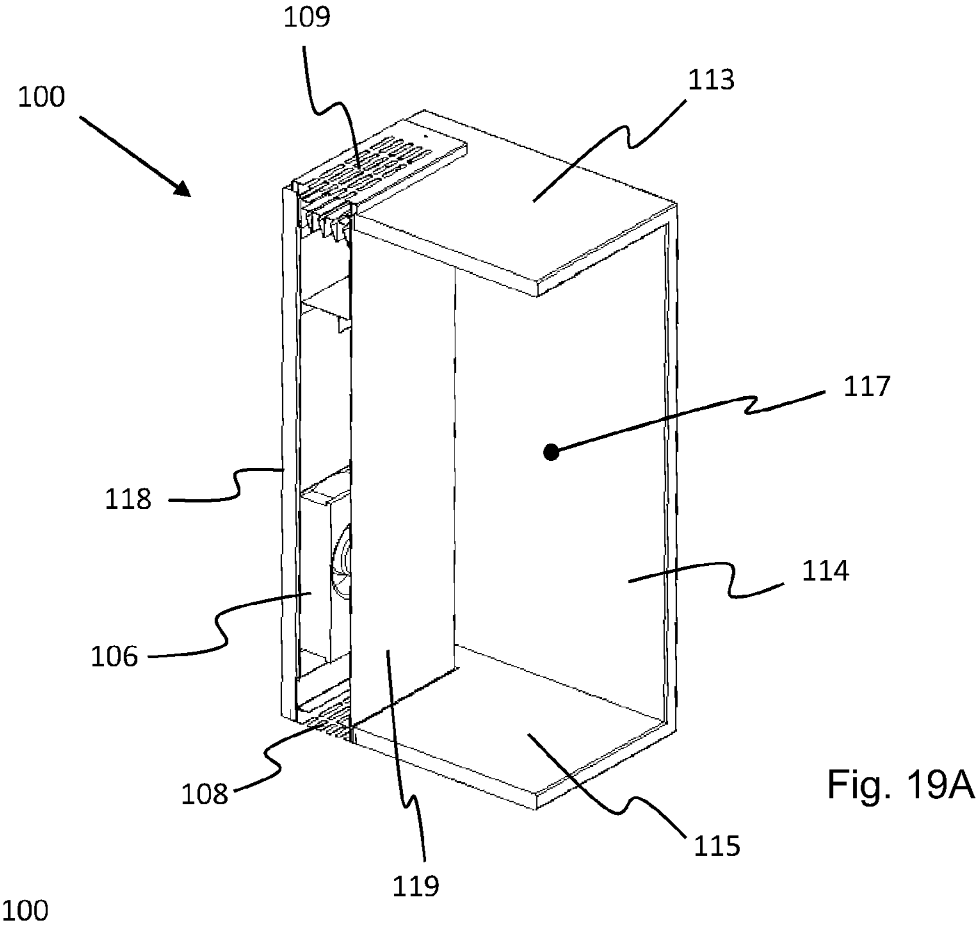
FIGS. 19A and 19B show an air sanitiser according to the invention which is integrated into a wall cabinet.
Figure 19B:
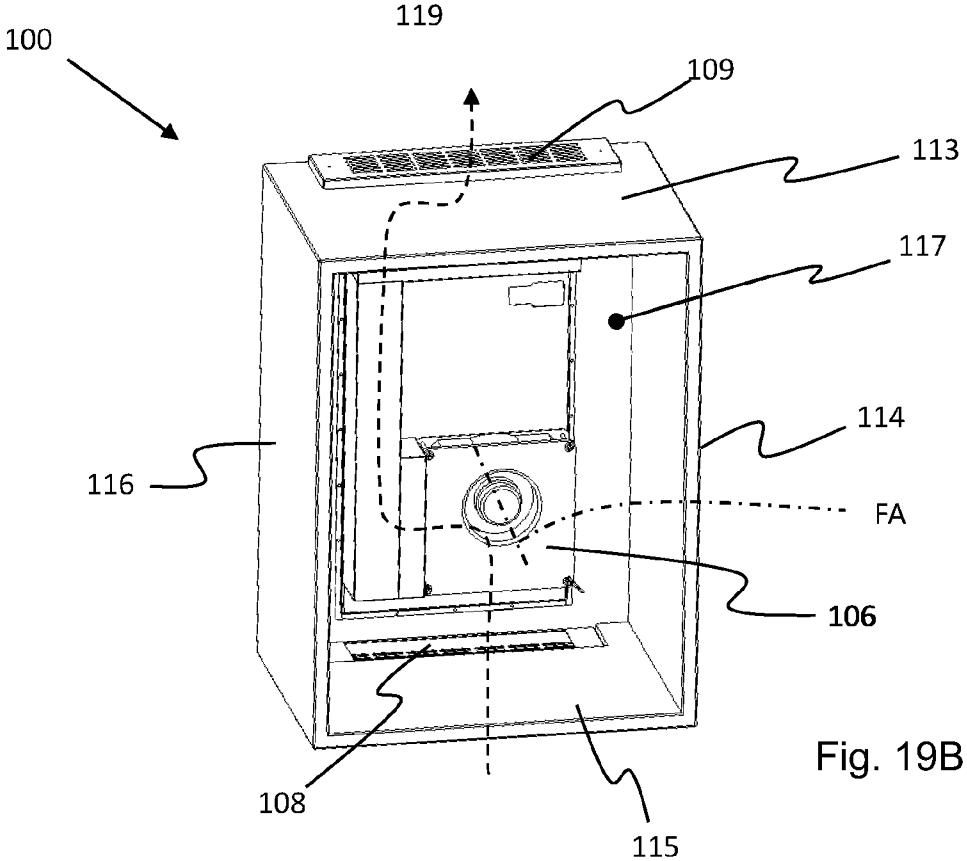

FIGS. 19A and 19B show an air sanitiser unit 100 that is designed in the manner of a (hanging) cabinet. The cabinet has side walls 113 to 116 that surround or define a cuboid-shaped free space 117. Furthermore, the cabinet has a double rear wall with two parallel walls 118 and 119 (cf. FIG. 19A), respectively, between which walls 118, 119 the actual air sanitiser is arranged, which preferably corresponds to the sanitising chamber 20 as described in connection with the extractor hood and thus can be devised accordingly as far as functional and constructional details are concerned.

Further reference may be made to the description of FIGS. 18A and 18B in order to avoid unnecessary repetition of text.

The dashed arrow in FIG. 19B indicates the path of the air flow.

Reference numeral FA in FIG. 19B denotes the fan axis.

The invention claimed is:

1. An extractor hood (1) for extracting vapour from a hob, said hood (1) adapted for being fitted above the hob and comprising:

a first part or extractor part (3) which is associated with a second part or flue (4) comprising an extractor unit or fan (5) which is connected to at least one exhaust aperture (8) of the second part or flue (4) for extracting the vapour; and a sanitising chamber (20) which treats air collected from an environment where the extractor hood (1) is placed, said sanitising chamber (20) comprising:

an extractor unit (21) to collect the air from the environment, a source of UV radiation (22) to sanitise the air, at least one exhaust aperture (23) to discharge the sanitised air; and an inner cavity (33) with a divider (46) which subdivides the inner cavity (33) into an extractor space (48) comprising the extractor unit (21) and a sanitising space (49) where the source of UV radiation (22) is located, the divider (46) having an aperture (47) which provides fluid communication between the extractor space (48) and the sanitising space (49);

wherein the source of UV radiation (22) is placed directly in the air flow path leading from the aperture (47) of the divider (46) to the sanitising chambers at least one exhaust aperture (23).

2. The extractor hood (1) according to claim 1, wherein said sanitising chamber (20) comprises a box-shaped body (32) having the inner cavity (33) which is delimited by a frontal portion (35), lateral walls (36), and a shoulder or rear portion (37), the frontal portion having an aperture (41) defined therein which permits entry of the air into the box-shaped body (32), and the at least one exhaust aperture (23) being provided on a different side or portion of said box-shaped body.

3. The extractor hood (1) according to claim 1, further comprising a filter (54) for the air at said exhaust aperture (23).

4. The extractor hood (1) according to claim 1, wherein the extractor unit (21) of the sanitising chamber is an electric fan (43), and the source of UV radiation comprises ultraviolet LED sources or at least one ultraviolet lamp.

5. The extractor hood (1) according to claim 4, wherein the lamp or the LED sources emit UVC radiation with wavelengths in a range of 200 and 285 nm.

6. The extractor hood (1) according to claim 4, the source of ultraviolet radiation comprises LEDs which emit UVA radiation with wavelengths in a range of 315 and 415 nm or UVB radiation with wavelengths in a range of 285 and 315 nm.

7. The extractor hood (1) according to claim 1, wherein the source of UV radiation comprises at least one LED lamp (22A, 22B) or LED bars (22C, 22D, 22E, 22F, 22G).

8. The extractor hood (1) according to claim 3, wherein said filter (54) comprises a part (54B) which faces the LED bars.

9. The extractor hood (1) according to claim 2, wherein the walls of the inner cavity (33) have a mirror finish.

10. The extractor hood (1) according to claim 2, further comprising a grid (42) over the aperture (41), or the aperture (41) is defined by a plurality of holes (42K) provided inside the frontal portion (35) of the box-shaped body (32) of the sanitising chamber.

11. The extractor hood (1) according to claim 1, wherein the sanitising chamber (20) is associated with one of the first or second parts (3, 4).

12. The extractor hood (1) according to claim 11, wherein said sanitising chamber (20) is secured on the second part or flue (4).

13. The extractor hood (1) according to claim 1, wherein the sanitising chamber (20) is placed inside or integrated with the second part or flue (4).

14. The extractor hood (1) according to claim 1, wherein the sanitising chamber (20) is placed transversely to the second part or flue (4) of the extractor hood, and an aperture for entry of the air into the sanitising chamber (20) and the at least on exhaust aperture (23) of the sanitising chamber (20) are placed in opposite sides (75, 76) of the sanitising chamber (20), such that the air treated moves orthogonally to the exhaust for the vapour extracted by the extractor hood (1).

15. The extractor hood (1) according to claim 1, wherein the sanitising chamber (20) is placed transversely to the second part or flue (4) of the extractor hood, such that the air treated moves orthogonally to the exhaust for the vapour extracted by the extractor hood (1), and an aperture for entry of the air into the sanitising chamber (20) and the at least one exhaust aperture (23) of the sanitising chamber (20) are placed on opposite sides with respect to the flue (4).

16. The extractor hood (1) according to claim 14, wherein the sanitising chamber (20) is placed on an upper side (3*a*) of the first part (3), said upper side (3*a*) facing away from said hob in an installed state of the extractor hood (1).

17. The extractor hood (1) according to claim 16, wherein the aperture (41) for entry of the air into the sanitising chamber (20) and the at least one exhaust aperture (23) of the sanitising chamber (20) are both placed in an upper side (20*a*) of the sanitising chamber (20), and said upper side (20*a*) of the sanitising chamber faces away from said upper side (3*a*) of the first part (3).

18. The extractor hood (1) according to claim 1, wherein the extractor hood (1) is configured as a ceiling hood and has an underside (3*b*) of said first part or extractor part (3), said underside (3*b*) is adapted to face a cooking hob in an installed state of the extractor hood (1) and presents at least one entry aperture (89) for the vapour, and the sanitising chamber (20) is integrated in said first part (3) on at least one side of the entry aperture (89), such that both an aperture (41) for entry of air to be sanitised and said at least one exhaust aperture (23) are on said underside (3*b*).

19. The extractor hood (1) according to claim 1, further comprising a power supply for the sanitiser chamber (20) that is independent and functions separately from a power supply of the extractor hood, such that simultaneous use of the extractor hood (1) and the sanitiser chamber (20) is prevented by respective controllers thereof.

20. An air sanitiser (100), comprising:

an air inlet (108) and an air outlet (109), said air inlet (108) and said air outlet (109) are connected by an air conduit in which a fan (106) is located for drawing in air through the inlet (108) and for discharging air from the outlet (109), at least one source of UV radiation (107) for sanitising the air is located in said conduit, the fan (106) comprises an impeller that is rotatable around a fan axis, such that the air is drawn in along said fan axis and discharged orthogonally with respect to said axis, and the source of UV radiation (107) is located downstream of said fan (106), said air sanitizer (100) being integrated into a housing or cabinet, said housing or cabinet having a plurality of side walls (101-104; 113-116), a front wall (105) and a back wall (118, 119), wherein the inlet (108) and the outlet (109) are arranged in the front wall (105).

21. The air sanitiser (100) according to claim 20, further comprising a mechanical filter inserted in the air inlet (108) to reduce fouling of the source of UV radiation (107).

22. The air sanitiser (100) according to claim 20, wherein said cabinet or housing is configured for fixing to a ceiling or wall of a room.

* * * * *